United States Patent
Hong et al.

(10) Patent No.: US 10,772,910 B2
(45) Date of Patent: Sep. 15, 2020

(54) GRAPHENE NANOSTRUCTURE-BASED PHARMACEUTICAL COMPOSITION FOR PREVENTING OR TREATING NEURODEGENERATIVE DISEASES

(71) Applicants: Seoul National University R&DB Foundation, Seoul (KR); The Johns Hopkins University, Baltimore, MD (US)

(72) Inventors: Byung Hee Hong, Seoul (KR); Je Min Yoo, Seoul (KR); Hanseok Ko, Lutherville, MD (US); Donghoon Kim, Baltimore, MD (US)

(73) Assignees: Seoul National University R&DB Foundation, Seoul (KR); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/004,744

(22) Filed: Jun. 11, 2018

(65) Prior Publication Data

US 2018/0289646 A1    Oct. 11, 2018

Related U.S. Application Data

(62) Division of application No. 15/301,853, filed as application No. PCT/KR2015/003385 on Apr. 3, 2015, now abandoned.

(30) Foreign Application Priority Data

Apr. 4, 2014    (KR) .................. 10-2014-0040400

(51) Int. Cl.
*A61K 33/44*        (2006.01)
*A61P 25/28*        (2006.01)
(Continued)

(52) U.S. Cl.
CPC ............ *A61K 33/44* (2013.01); *A61K 31/194* (2013.01); *A61K 41/0052* (2013.01);
(Continued)

(58) Field of Classification Search
CPC ......... A61K 33/44; A61P 25/28; C01B 32/15; C01B 32/182; C01B 32/198; C01B 2204/00
See application file for complete search history.

(56) References Cited

U.S. PATENT DOCUMENTS 7,163,956 B2    1/2007  Wilson et al.
2007/0122463 A1   5/2007  Ko et al.
(Continued)

FOREIGN PATENT DOCUMENTS

KR    10-2008-0033463    4/2008
KR    10-2009-0019790    2/2009
(Continued)

OTHER PUBLICATIONS

Li et al. (Advanced Materials, 2012, 24, 1722-1728) (Year: 2012).*
(Continued)

*Primary Examiner* — Theodore R. West
(74) *Attorney, Agent, or Firm* — Fish & Richardson P.C.

(57) ABSTRACT

The present disclosure relates to a pharmaceutical composition for preventing or treating neurodegenerative diseases, the pharmaceutical composition including a graphene nanostructure as an active ingredient.

14 Claims, 20 Drawing Sheets

(51) Int. Cl.
| | |
|---|---|
| C01B 32/182 | (2017.01) |
| A61K 41/00 | (2020.01) |
| A61K 31/194 | (2006.01) |
| A61K 49/00 | (2006.01) |
| A61N 5/06 | (2006.01) |
| A61N 5/067 | (2006.01) |

(52) U.S. Cl.
CPC ...... A61K 49/0021 (2013.01); A61K 49/0052 (2013.01); A61N 5/062 (2013.01); C01B 32/182 (2017.08); A61N 2005/066 (2013.01); A61N 2005/067 (2013.01); C01B 2204/32 (2013.01)

(56) References Cited

U.S. PATENT DOCUMENTS

| | | |
|---|---|---|
| 2015/0064720 A1 | 3/2015 | Chen et al. |
| 2016/0193249 A1* | 7/2016 | Tour ................. A61K 33/44 424/489 |

FOREIGN PATENT DOCUMENTS

| | | | |
|---|---|---|---|
| KR | 10-2013-0122585 | 11/2013 | |
| WO | WO 2013/066398 | 5/2013 | |
| WO | WO-2013066398 A1 * | 5/2013 | ............... B82Y 5/00 |
| WO | WO 2013/148341 | 10/2013 | |
| WO | WO 2015/034930 | 3/2015 | |

OTHER PUBLICATIONS

Kovtyukhova et al. (Chem Mater, 1999, 11, 771-778) (Year: 1999).*
Henning (Fine, Specialty, & Performance Chemicals, Jun. 2002) http://citeseerx.ist.psu.edu/viewdoc/download;jsessionid=E49081D31E822F69597819400C46C22D?doi=10.1.1.604.3999&rep=rep1&type=pdf). (Year: 2002).*
U.S. 15/301,853, filed Mar. 23, 2017, Hong et al.
International Search Report of PCT/KR2015/003385 dated Jun. 30, 2015 (3 pages).
Li et al., Using Graphene Oxide High Near-Infrared Absorbance for Photothermal Treatment of Alzheimer's Disease, Advanced Materials, 24(13):1722-1728 (2012).
Peng et al., Graphene Quantum Dots Derived from Carbon Fibers, NANO Letters 12:844-849 (2012).
Shim et al., Analysis of zinc oxide nanoparticles binding proteins in rat blood and brain homogenate, International Journal of Nanomedicine, 9(Suppl 2):217-224 (2014).
Son et al. Emissive ZnO-gmphene quantum dots for white-light-emitting diodes, Nature Nanotechnology, 7:465-471 (2012) (published online May 27, 2012).
Varela et al., Leptin and insulin pathways in POMC and AgRP neurons that modulate energy balance and glucose homeostasis, EMBO reports, 13(12):1079-1086 (2012).
Alam et al., Revealing the tunable photoluminescence properties of graphene quantum dots, J. Mater. Chem. C., 2:6954 (2014).
Dong et al., Blue luminescent graphene quantum dots and graphene oxide prepared by tuning the carbonization degree of citric acid, Carbon 50:4738-4743 (2012).
EP Communication for App No. 15774194.3, dated Jan. 2, 2019 (4 pages).
Hu et al., Quantum-Dot-Tagged Reduced Graphene Oxide Nanocomposites for Bright Fluorescence Bioimaging and Photothermal Therapy Monitored In Situ, Adv. Mater. 24:1748-1754 (2012).
JP Office Action for App No. JP 2017-503755, dated Dec. 26, 2018 (with English Translation) (6 pages).
Maezawa et al., Congo red and thioflavin-T analogs detect A[beta] oligomers., J. Neurochem., 104(2):457-468 (Jan. 2008).
Mahmoudi et al., Graphene oxide strongly inhibits amyloid beta fibrillation, Nanoscale, 4(23);7322 (Jan. 2012).
Kim et al., Two Dimensional Soft Material: New Faces of Graphene Oxide, Acc Chem Res. 45(8):1356-64 Aug. 2012.
Zeng et al., Unraveling the cooperative synergy of zerodimensional graphene quantum dots and metal nanocrystals enabled by layer-by-layer assembly, J. Mater. Chem A., 6:1700 (2018).
Kim et al., Graphene quantum dots prevent α-synucleinopathy in Parkinson's disease, Nature Nanotechnology, 13:812-818 (2018).
Kim et al., Supplementary Information—Graphene quantum dots prevent α-synucleinopathy in Parkinson's disease, Nature Nanotechnology, 13:812-818 (2018) [29 pages].

* cited by examiner

PL: WEAK (INTERMEDIATE) PHOTOLUMINESCENCE AT 491 & 547 NM

FT-IR: 1724 cm$^{-1}$: CARBOXYLATE GROUP
1614 cm$^{-1}$: AROMATIC C=C PEAK

FIG. 6B
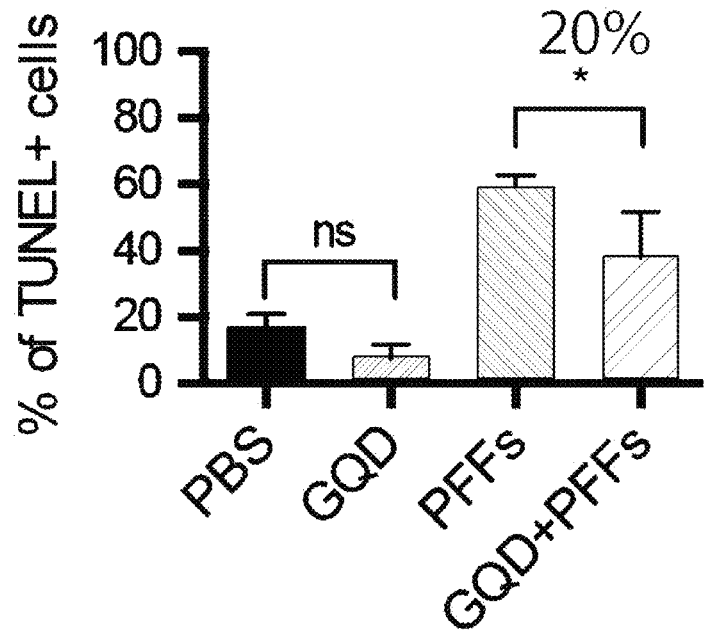
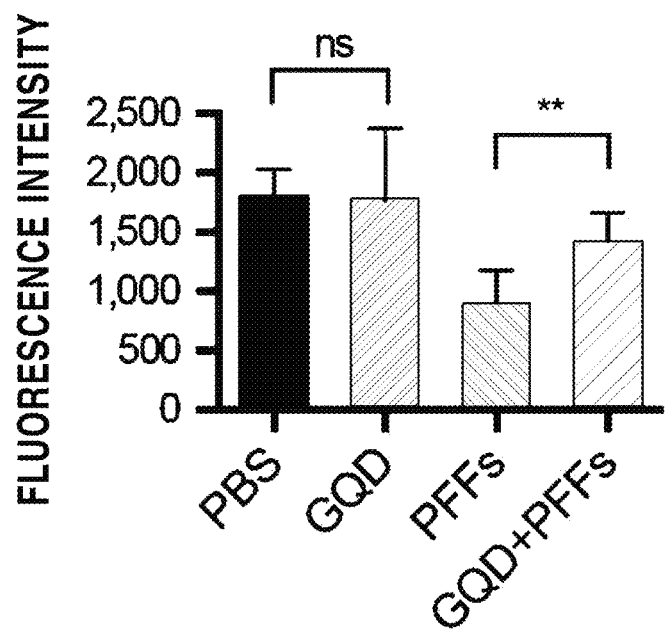

FIG. 7B
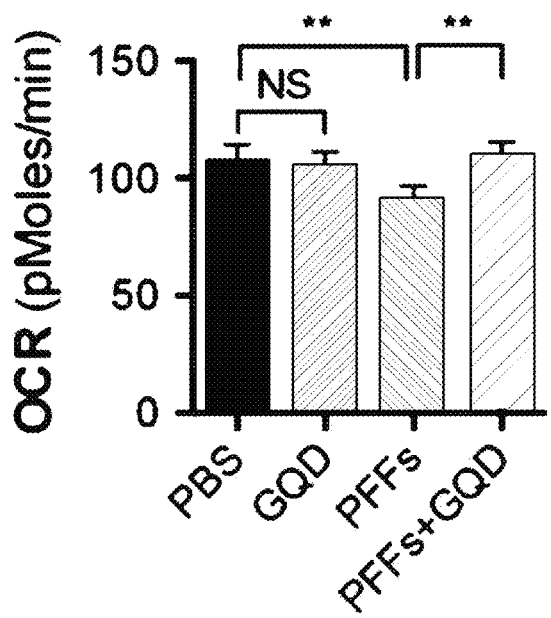
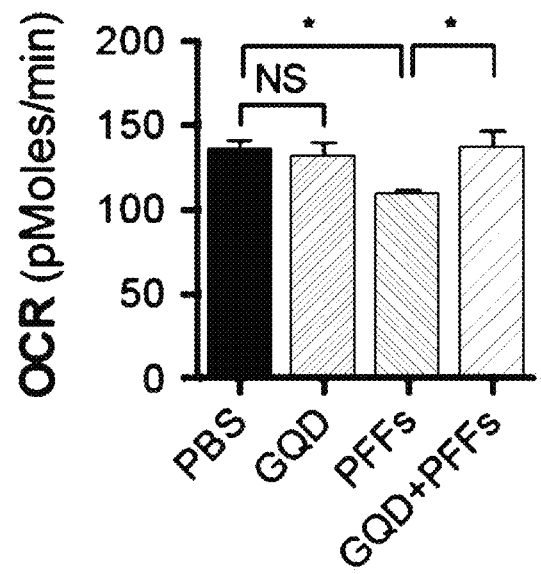
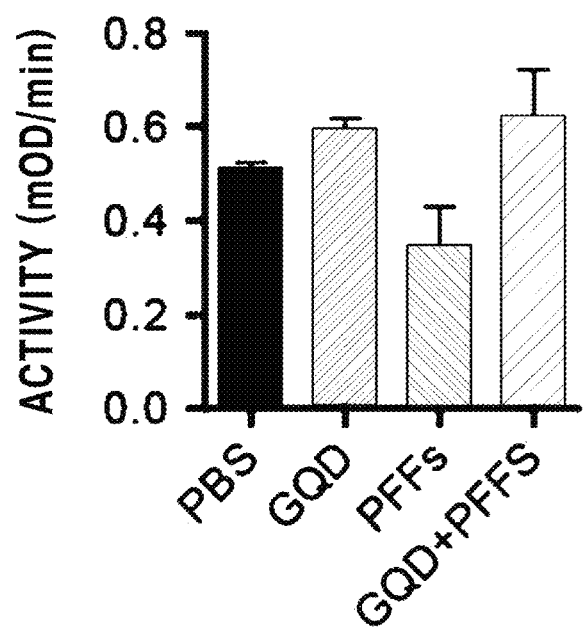

(a)-(b): PFFS AFTER INCUBATION AT 37°C FOR 3 HOURS
(c)-(d): PFFS +GQD AFTER INCUBATION AT 37°C FOR 3 HOURS (a)-(d): PFFS +GQD AFTER INCUBATION AT 37°C FOR 3 HOURS

FIG. 13
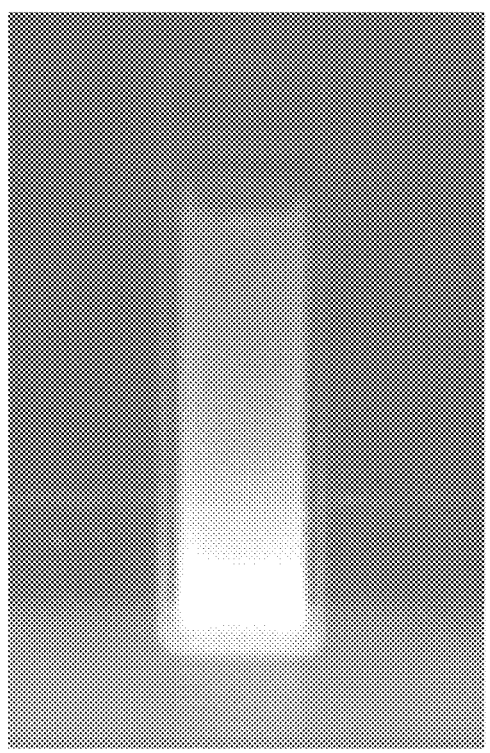
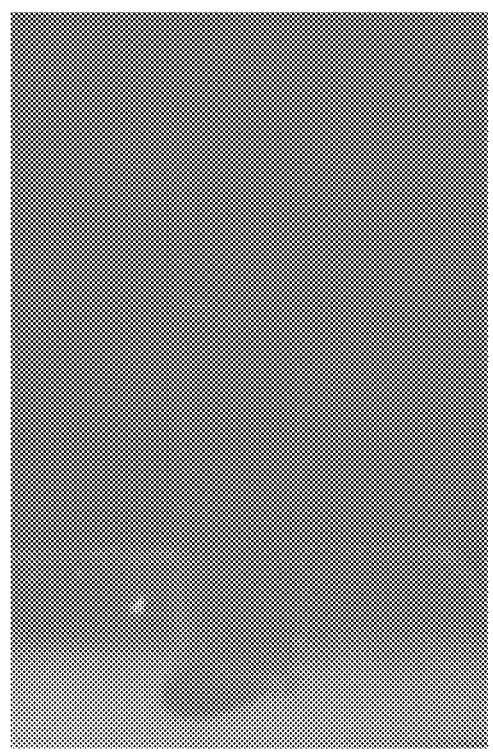
GQD           CONGO RED

GRAPHENE NANOSTRUCTURE-BASED PHARMACEUTICAL COMPOSITION FOR PREVENTING OR TREATING NEURODEGENERATIVE DISEASES

TECHNICAL FIELD

The present invention relates to a pharmaceutical composition for preventing or treating neurodegenerative diseases, the pharmaceutical composition including a graphene nanostructure as an active ingredient.

BACKGROUND

It has been known that protein misfolding causes normal proteins to lose their function and abnormal proteins to be accumulated in cells and produce toxicity and thus causes various diseases such as Alzheimer's disease, Parkinson's disease, Huntington's chorea, Lou Gehrig's disease, cancer, cystic fibrosis, and type II diabetes. That is, malfunction of proteostasis causes protein misfolding and its intracellular abnormal accumulation.

All the causes of neurodegenerative diseases have not yet been found, but it has been well known that aggregation of neuronal proteins is a main cause. Fibrillated proteins are gradually transmitted to adjacent neurons and finally necrose all the neurons in a specific part of the brain, so that the specific part cannot perform its functions. As for Parkinson's disease, the disease progresses while neurons that produce a neurotransmitter called dopamine are gradually necrosed. Sinemet is now the most common drug prescribed to Parkinson's disease patients, and Sinemet and other Parkinson's disease drugs do not function to fundamentally treat or delay the disease but supply Levodopa (L-DOPA) which is converted into dopamine in neurons to temporally reduce the symptoms. In the end, as the disease continues to progress, the effect of the drugs decreases, which causes death.

As one of anti-amyloid compounds researched relating to protein misfolding, Congo Red has an effect of inhibiting fibril formation caused by protein misfolding but is highly toxic to the body and cannot function to inhibit transition of misfolded proteins and thus delay the progress of a disease. Further, a conventional drug is formulated into a specific shape with a uniform size and thus does not have any particular advantage in the treatment of a disease in terms of entropy.

Accordingly, a lot of studies have been carried out to treat protein misfolding (Korean Patent Laid-open Publication No. 10-2009-0019790), but there has been no great achievement about a drug which is not toxic to the body but has an excellent inhibitory activity.

DISCLOSURE OF THE INVENTION

Problems to be Solved by the Invention

Accordingly, the present disclosure provides a pharmaceutical composition for preventing or treating neurodegenerative diseases, the pharmaceutical composition including a graphene nanostructure as an active ingredient.

However, problems to be solved by the present disclosure are not limited to the above-described problems. Although not described herein, other problems to be solved by the present disclosure can be clearly understood by those skilled in the art from the following descriptions.

Means for Solving the Problems

In accordance with a first aspect of the present disclosure, there is provided a pharmaceutical composition for preventing or treating neurodegenerative diseases, the pharmaceutical composition including a graphene nanostructure as an active ingredient.

Effects of the Invention

According to the exemplary embodiments of the present disclosure, the pharmaceutical composition for preventing or treating neurodegenerative diseases, the pharmaceutical composition including a graphene nanostructure as an active ingredient is the first attempt to use a graphene nanostructure for preventing and treating neurodegenerative diseases. The graphene nanostructure is not toxic to the body and not accumulated in the body, but it has an excellent effect such as inhibiting fibril formation caused by protein misfolding to 80% and is effective in inhibiting transition of misfolded proteins and thus delaying the progress of a disease. Further, unlike the conventional drug, the graphene nanostructure is not limited to a specific shape and the graphene nanostructures are different from each other in molecular weight, molecular formula, and shape, which inhibits formation of crystals in terms of entropy, and, thus, it is possible to fundamentally treat a disease. Furthermore, the graphene nanostructure exhibits fluorescence in a UV-vis range, and it is possible to track movement of the graphene nanostructure to act as a drug in the body by appropriately regulating the intensity of fluorescence. Also, it is possible to track a neuronal protein by bonding a material targeting the neuronal protein to a terminal functional groups of the graphene nanostructure. As such, the graphene nanostructure may be induced to a place near the neuronal protein and then a far-infrared laser less damaging a cell may be irradiated, so that fibrillation and aggregation can be inhibited by a photothermal effect of the graphene nanostructure.

BRIEF DESCRIPTION OF THE DRAWINGS

FIG. 6A and FIG. 6B provide (A) images and (B) graphs showing the result of analysis of a neuron survival rate affected by a graphene nanostructure in accordance with an example of the present disclosure.

FIG. 7A and FIG. 7B provide (A) images and (B) graphs showing the result of analysis of 8-OHG staining which shows a reactive oxygen species generation inhibitory activity of a graphene nanostructure in accordance with an example of the present disclosure.

FIG. 13 provides images showing luminescent characteristics of a graphene nanostructure and Congo Red in accordance with an example of the present disclosure.

MODE FOR CARRYING OUT THE INVENTION

Figure 1:
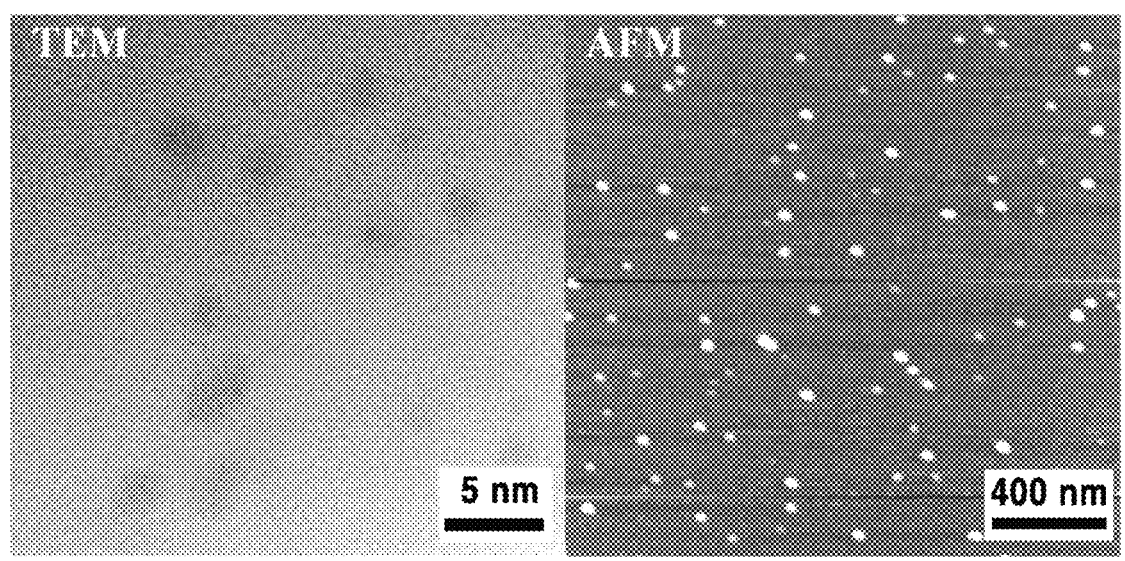
FIG. 1 shows TEM and AFM images of graphene quantum dots in accordance with an example of the present disclosure.

Hereinafter, embodiments and examples of the present disclosure will be described in detail with reference to the accompanying drawings so that the present disclosure may be readily implemented by those skilled in the art.

However, it is to be noted that the present disclosure is not limited to the embodiments and examples but can be embodied in various other ways. In drawings, parts irrelevant to the description are omitted for the simplicity of explanation, and like reference numerals denote like parts through the whole document.

Through the whole document, the term "on" that is used to designate a position of one element with respect to another element includes both a case that the one element is adjacent to the another element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise. Through the whole document, the term "about or approximately" or "substantially" are intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, the term "graphene quantum dots (GQDs)" refers to nano-sized fragments of graphene oxides or reduced graphene oxides.

Through the whole document, the term "graphene" refers to a material forming a polycyclic aromatic molecule with multiple carbon atoms covalently bonded to each other. The covalently bonded carbon atoms form a six-member ring as a repeating unit, but can further include a five-member ring and/or a seven-member ring.

Through the whole document, the term "graphene oxide" may be abbreviated as "GO", and may include a structure in which a functional group containing oxygen such as a carboxyl group, a hydroxyl group, or an epoxy group is bonded onto graphene, but may not be limited thereto.

Through the whole document, the term "reduced graphene oxide" refers to graphene oxide decreased in a percentage of oxygen through a reduction process and may be abbreviated as "rGO", but may not be limited thereto.

Hereinafter, the exemplary embodiments of the present disclosure will be described in detail, but the present disclosure may not be limited thereto.

In accordance with a first aspect of the present disclosure, there is provided a pharmaceutical composition for preventing or treating neurodegenerative diseases, the pharmaceutical composition including a graphene nanostructure as an active ingredient.

In accordance with an exemplary embodiment of the present disclosure, the pharmaceutical composition may further include a pharmaceutically acceptable carrier or excipient, but may not be limited thereto. The pharmaceutically acceptable carrier or excipient is not limited as long as it can be used in a pharmaceutical composition, and may include a member selected from the group consisting of, for example, vaseline, lanolin, polyethylene glycol, alcohol, and combinations thereof, but may not be limited thereto.

In accordance with an exemplary embodiment of the present disclosure, the neurodegenerative diseases are relevant to protein misfolding, and may include a member selected from the group consisting of, for example, Alzheimer's disease, Parkinson's disease, Huntington's chorea, HIV dementia, stroke, senile systemic amyloidosis, primary systemic amyloidosis, secondary systemic amyloidosis, type II diabetes, amyotrophic amyloidosis, hemodialysis-related amyloidosis, transmissible spongiform encephalopathy, and multiple sclerosis, but may not be limited thereto.

In accordance with an exemplary embodiment of the present disclosure, the graphene nanostructure may include graphite, graphene, or graphene quantum dots, but may not be limited thereto.

The graphene quantum dots may have a size in the range of, for example, from about 1 nm to about 20 nm, from about 5 nm to about 20 nm, from about 10 nm to about 20 nm, from about 15 nm to about 20 nm, from about 1 nm to about 15 nm, from about 1 nm to about 10 nm, or from about 1 nm to about 5 nm, but may not be limited thereto.

In accordance with an exemplary embodiment of the present disclosure, the graphene nanostructure may include graphene nanostructures with various sizes in the range of from about 1 nm to about 100 nm, for example, from about 10 nm to about 100 nm, from about 30 nm to about 100 nm, from about 50 nm to about 100 nm, from about 70 nm to about 100 nm, from about 90 nm to about 100 nm, from about 1 nm to about 90 nm, from about 1 nm to about 70 nm, from about 1 nm to about 50 nm, from about 1 nm to about 30 nm, or from about 1 nm to about 10 nm, but may not be limited thereto.

In accordance with an exemplary embodiment of the present disclosure, the graphene nanostructure may inhibit fibril formation caused by protein misfolding, and also inhibit transition of misfolded proteins, but may not be limited thereto.

In accordance with an exemplary embodiment of the present disclosure, the graphene nanostructure is not accumulated in the body and not toxic to the body.

In accordance with an exemplary embodiment of the present disclosure, the graphene nanostructure may inhibit generation of reactive oxygen species in neurons through a mechanism that inhibits mitochondrial dysfunction caused by fibrillated proteins, but may not be limited thereto.

In accordance with an exemplary embodiment of the present disclosure, the pharmaceutical composition may include a material targeting a neuronal protein, for example, Congo Red as an anti-amyloid material or thioflavin T or S as an amyloid detecting dye, which is bonded to a terminal functional group of the graphene nanostructure, but may not be limited thereto.

The functional group according to the present disclosure may include oxygen atoms and may be —OH, —COOH, or —C=O, but may not be limited thereto.

In accordance with an exemplary embodiment of the present disclosure, the graphene nanostructure may show a photothermal effect upon irradiation of a far-infrared laser, but may not be limited thereto.

In accordance with an exemplary embodiment of the present disclosure, the pharmaceutical composition of the present disclosure has an advantage of being able to track a neuronal protein by bonding a material targeting the neuronal protein to a terminal functional groups of the graphene nanostructure. As such, the graphene nanostructure may be induced to a place near the neuronal protein and then a far-infrared laser less damaging a cell may be irradiated, so that fibrillation and aggregation can be inhibited by a photothermal effect of the graphene nanostructure.

MODE FOR CARRYING OUT THE INVENTION

Hereinafter, examples of the present disclosure will be described in more detail, but the scope of the present disclosure is not limited thereto.

EXAMPLES

Preparation Example 1

Figure 2:
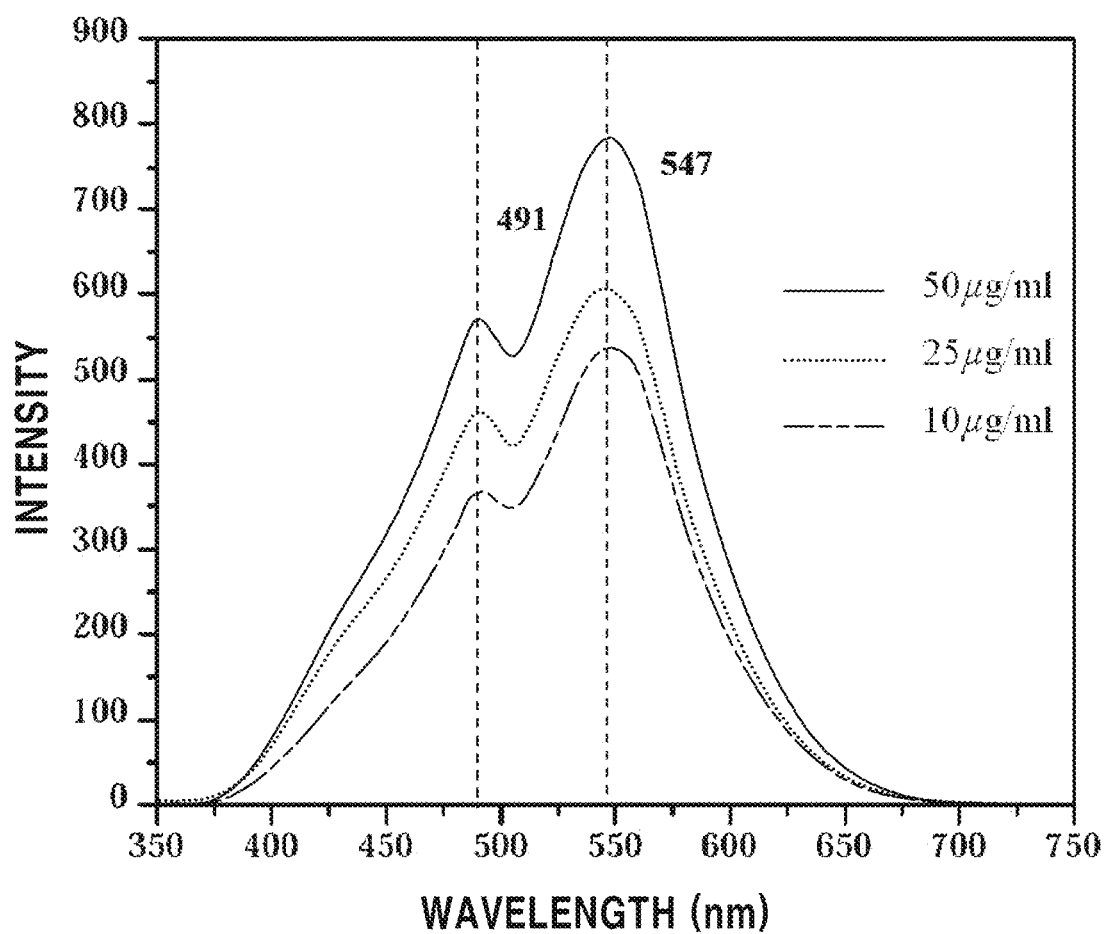
FIG. 2 is a graph showing the result of PL analysis on graphene quantum dots in accordance with an example of the present disclosure.
Figure 3:
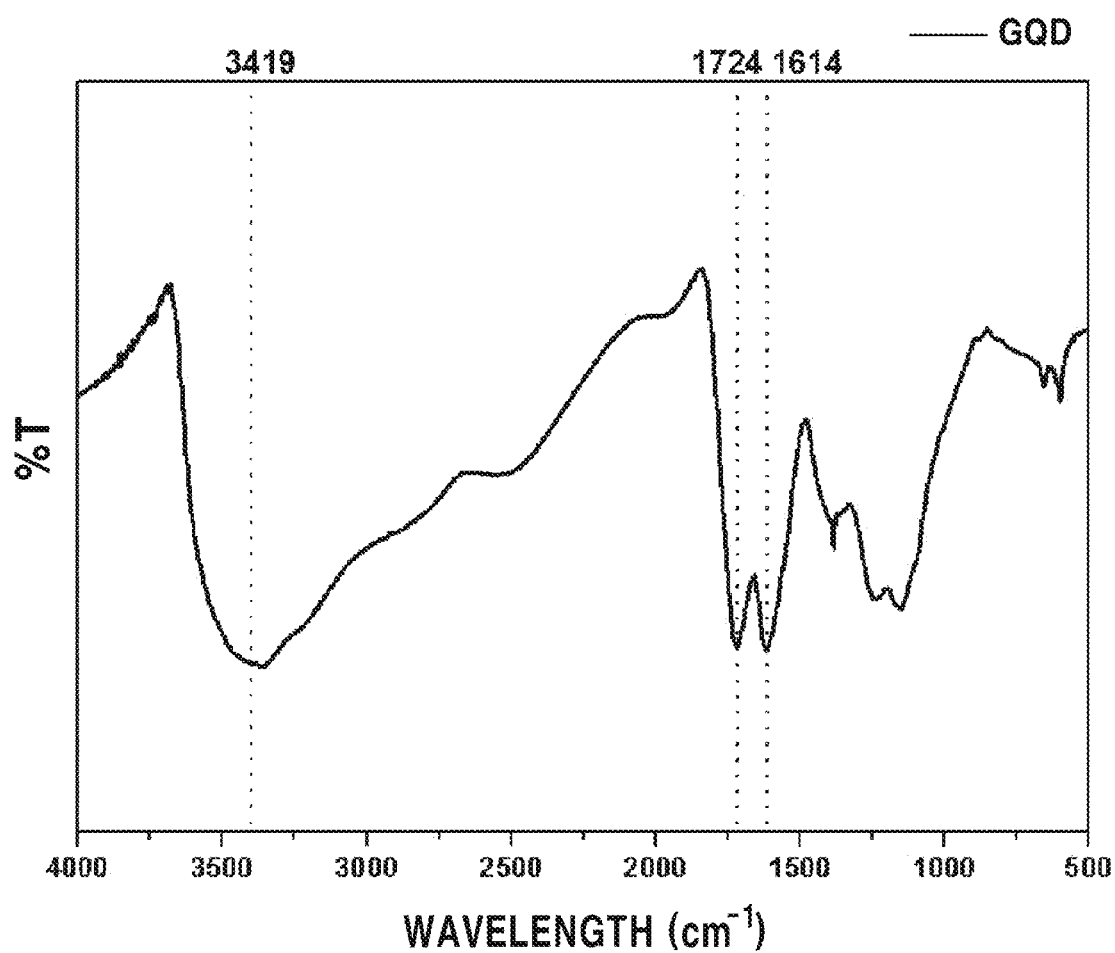
FIG. 3 is a graph showing the result of FT-IR analysis on graphene quantum dots in accordance with an example of the present disclosure.
Figure 4:
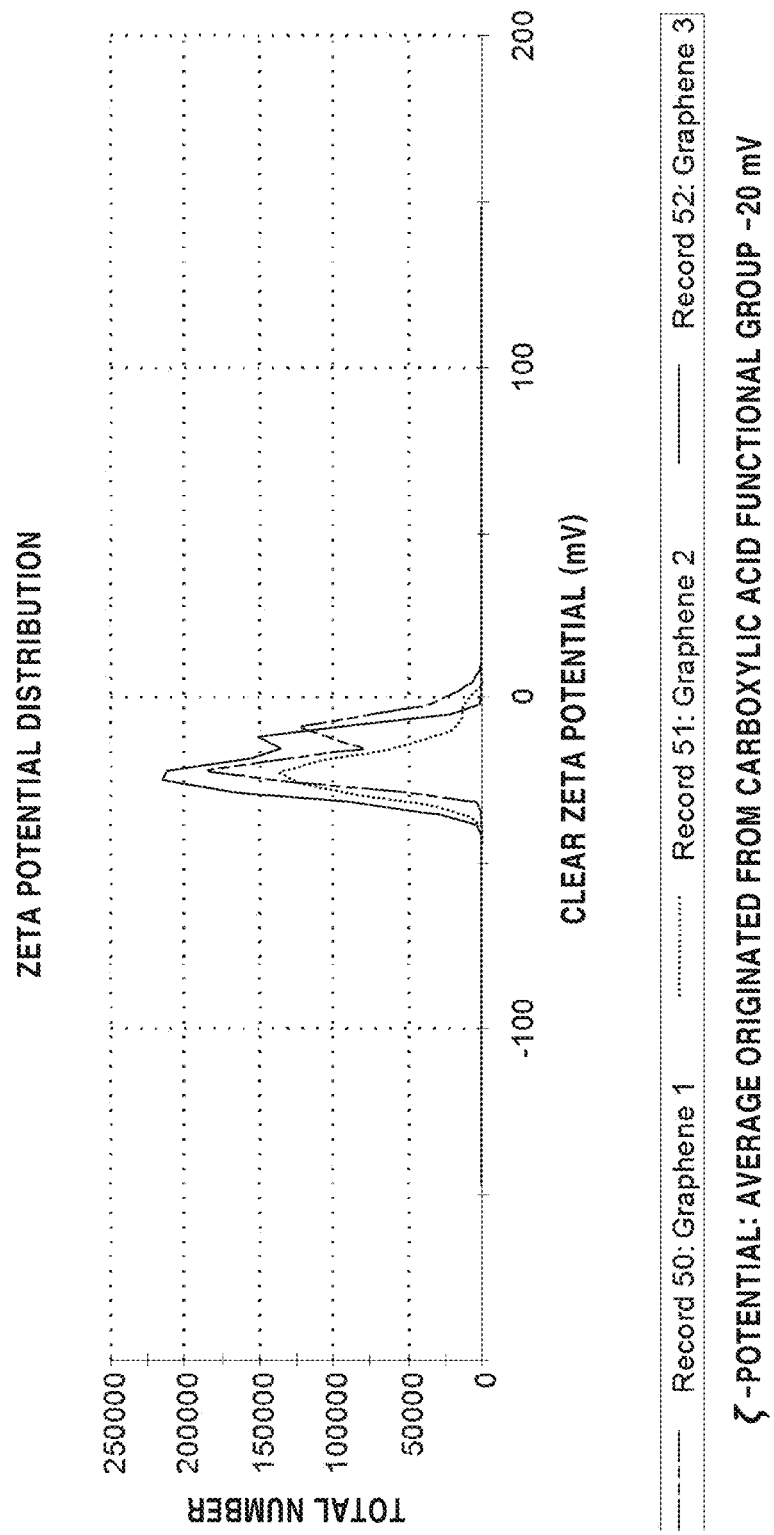
FIG. 4 is a graph showing the result of Zeta potential measurement on graphene quantum dots in accordance with an example of the present disclosure.

GQDs were prepared with reference to the article disclosed in Nano Letters 2012 [*Nano Lett,* 12, 844-849 (2012)]. A carbon fiber was put into a solution including a mixture of sulfuric acid and nitric acid at a ratio of 3:1 and then heated at 80° C. for 24 hours (thermo-oxidation process). After completion of the reaction, the product was purified through dialysis and vacuum filtration and GQDs in the form of powder were finally obtained using a Rotovap. The prepared GQDs were particles with structurally various sizes (about 5 nm to about 20 nm) (FIG. 1). The prepared GQDs had other characteristics such as exhibiting fluorescence under a UV lamp (Emission: 490 nm, and 550 nm) (JASCO FP-8300 Fluorescence Spectrometer) (FIG. 2) and showing a photothermal effect upon irradiation of 808 nm NIR laser. According to the FT-IR spectrum (Thermo Scientific Nicolet iS 10 FT-IR Spectrometer), a carboxyl group (—COOH) at a terminal of GQDs was observed at 1724 cm' and an aromatic C=C peak was observed at 1614 cm' (FIG. 3). A surface charge analyzed from Zeta potential (Malvern Zetasizer Nano ZS) was shown as about −20 mV (FIG. 4).

Preparation Example 2

A material in which Congo Red as a material targeting a neuronal protein was bonded to a terminal functional group of the prepared graphene nanostructure (GQDs) was prepared by a reaction as shown in the following Reaction Formula. Samples 1, 2, and 3 were prepared by applying different amounts of the Congo Red (100 μg/ml, 250 μg/ml, and 500 μg/ml), respectively:

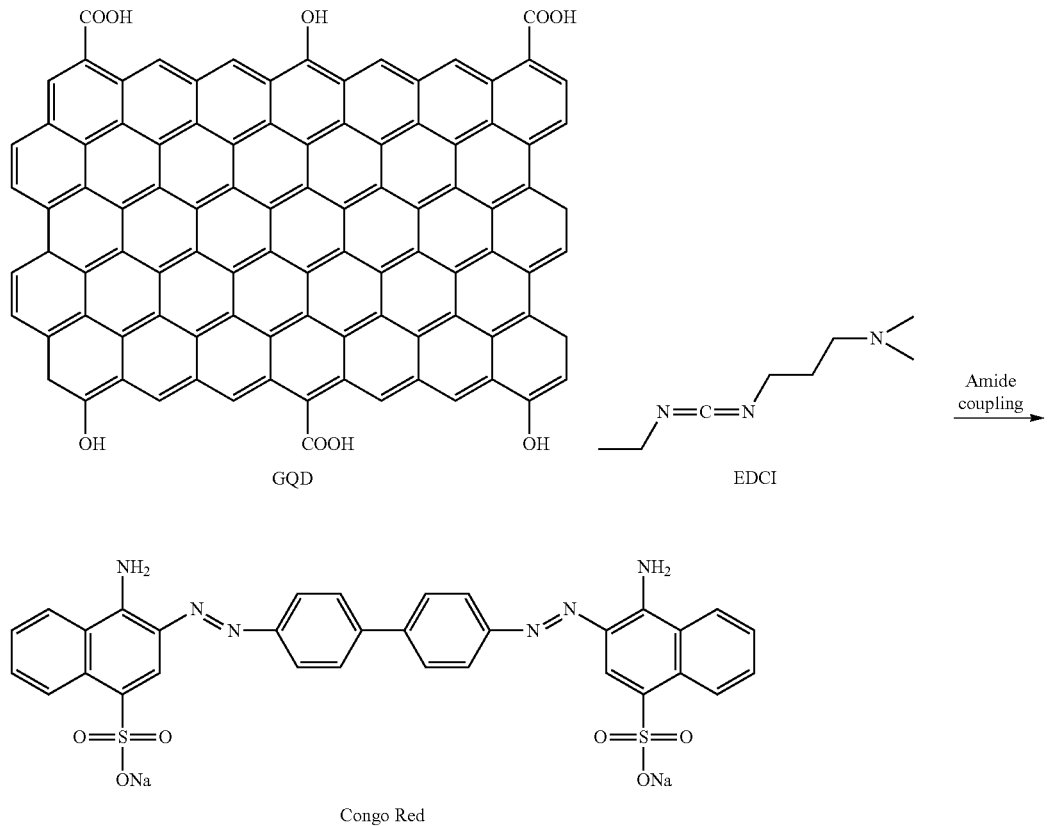

-continued

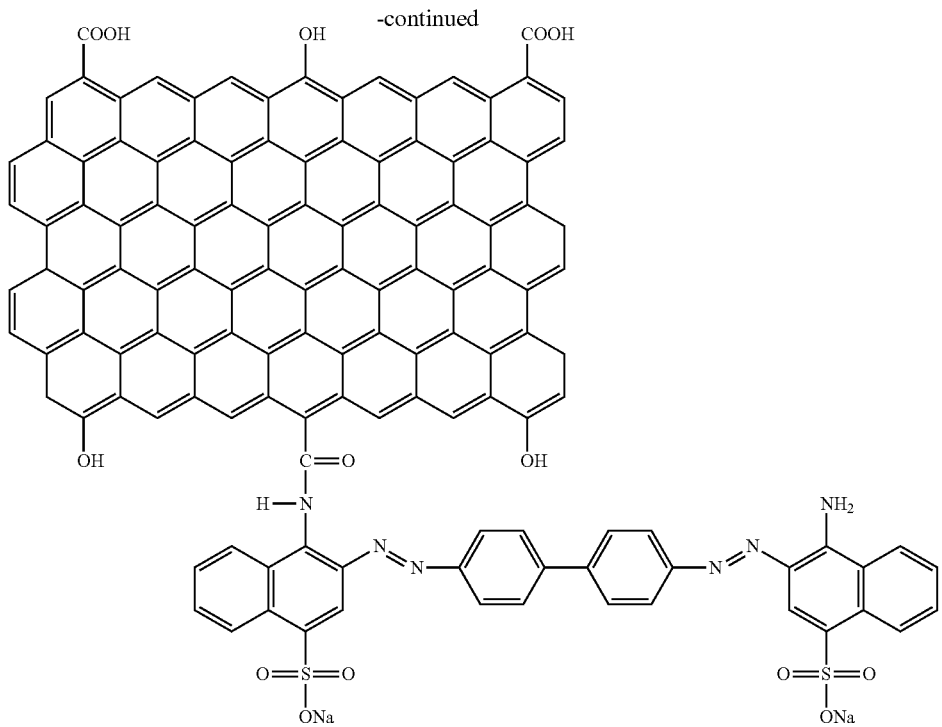

Test Example 1

Figure 5:
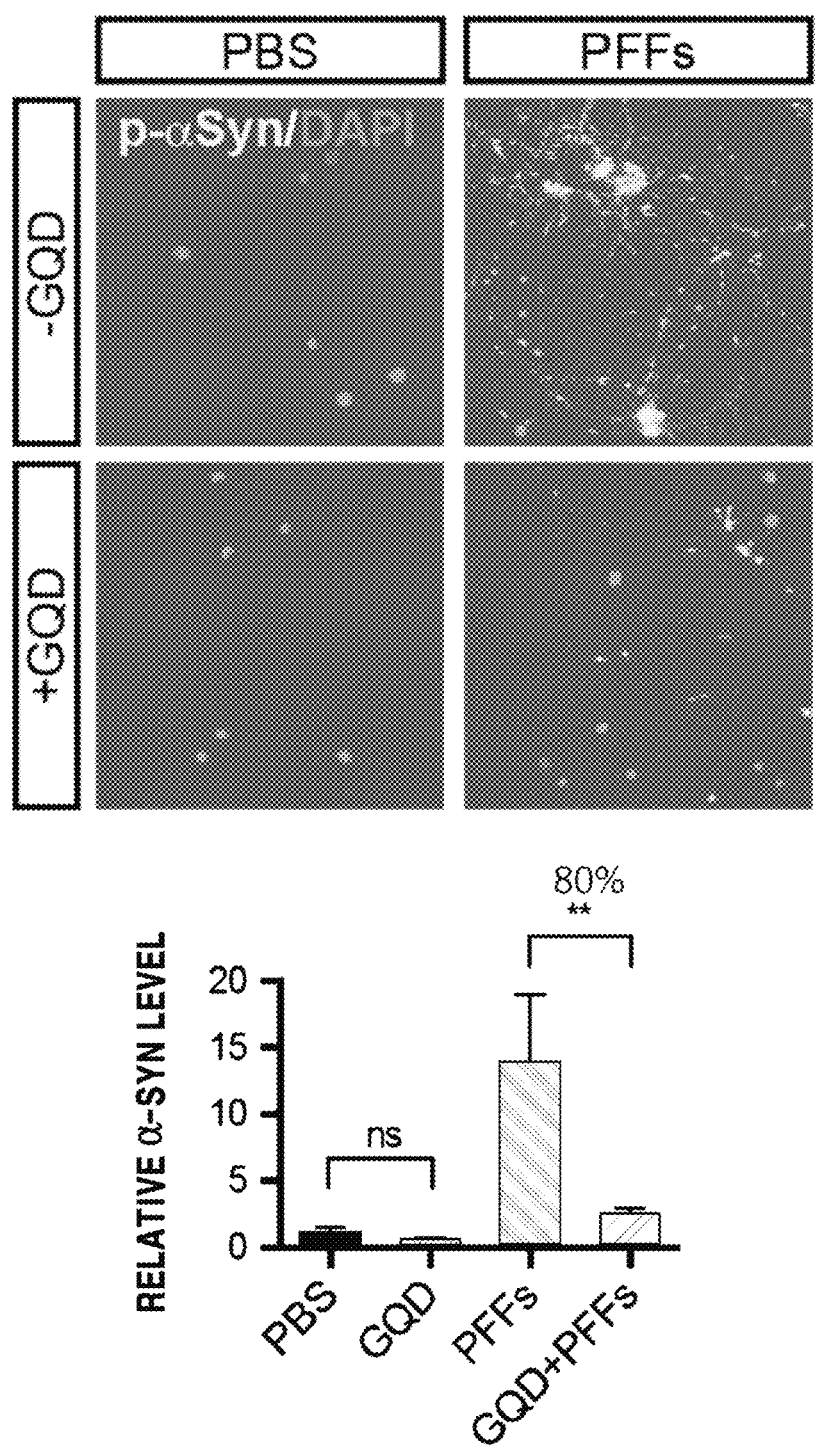
FIG. 5 shows a fibrillation inhibiting effect of a graphene nanostructure in accordance with an example of the present disclosure.
Figure 6A:
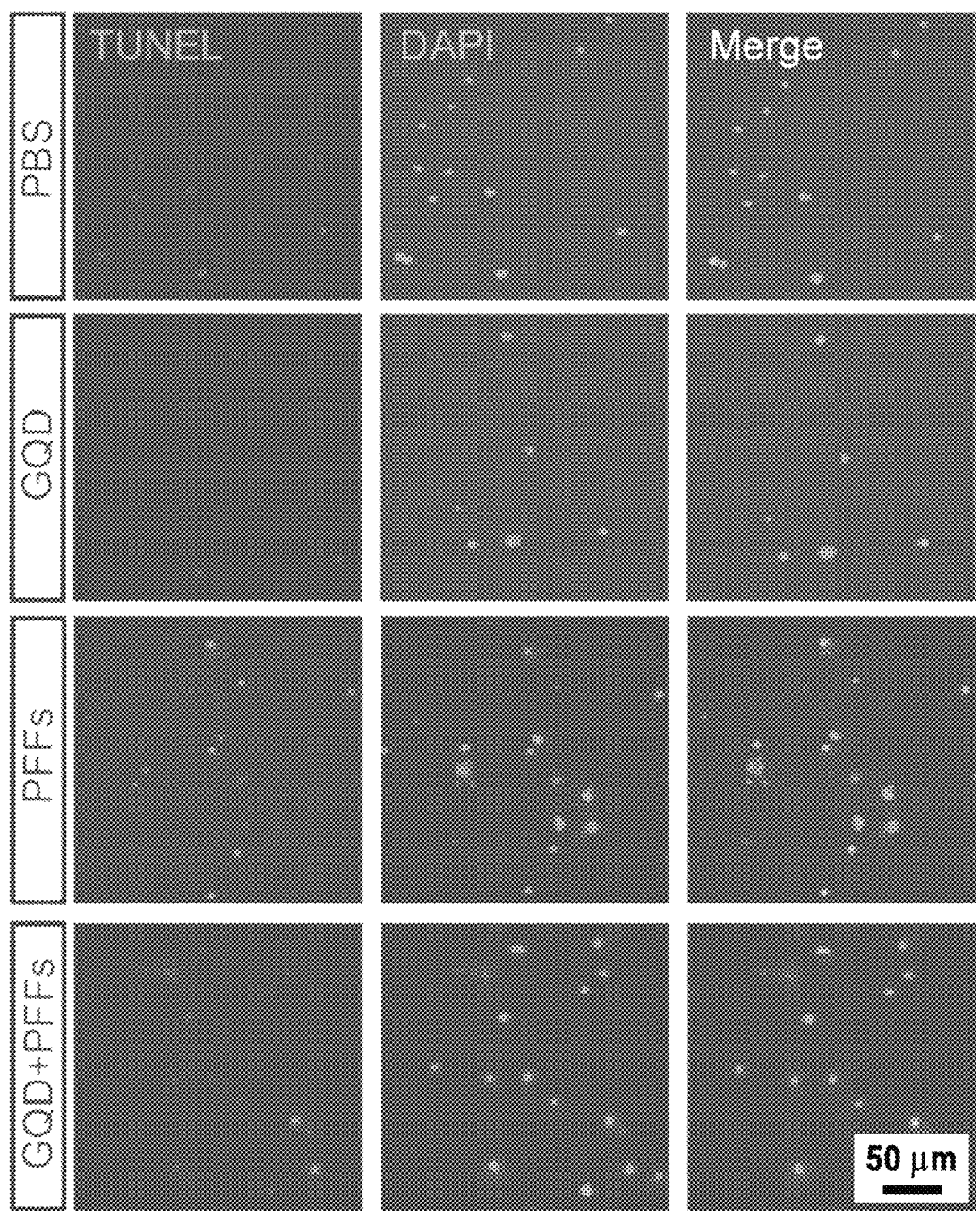

A fibrillation inhibition effect of a graphene quantum dot was determined using PFFs (pre-formed fibrils) as an alpha-synuclein test model. Specifically, fibrils were formed about a week after injection of the PFFs into neurons and finally caused necrosis of the neurons. Fibrillation causes phosphorylation of alpha-synuclein and can be recognized by staining as shown in FIG. 5. It was observed that p-a-syn (phosphorylated alpha-synuclei) were dense in response to injection of PFFs (1 µg/mL) only, but upon injection of GQDs (1 µg/mL), the p-a-syn (phosphorylated alpha-synuclei) almost disappeared to the level that nothing was injected (FIG. 5). As can be seen from FIG. 5, the p-a-syn was reduced to about 80%, which can be practically considered that fibrillation is almost entirely inhibited. Further, a neuron survival rate increases by about 20% (FIG. 6B). A neuron survival rate (analyzed by TUNEL screening) in case of injecting GQDs only was higher than a case where only a PBS medium was injected, and, thus, it was confirmed that the GQDs were not toxic to neurons (FIG. 6A and FIG. 6B). The left images of FIG. 6A show TUNNEL screening in which a damaged cell is stained red, the middle images show DAPI staining in which DNA in a cell nucleus is stained blue, and the right images show quantification thereof.

Figure 7A:
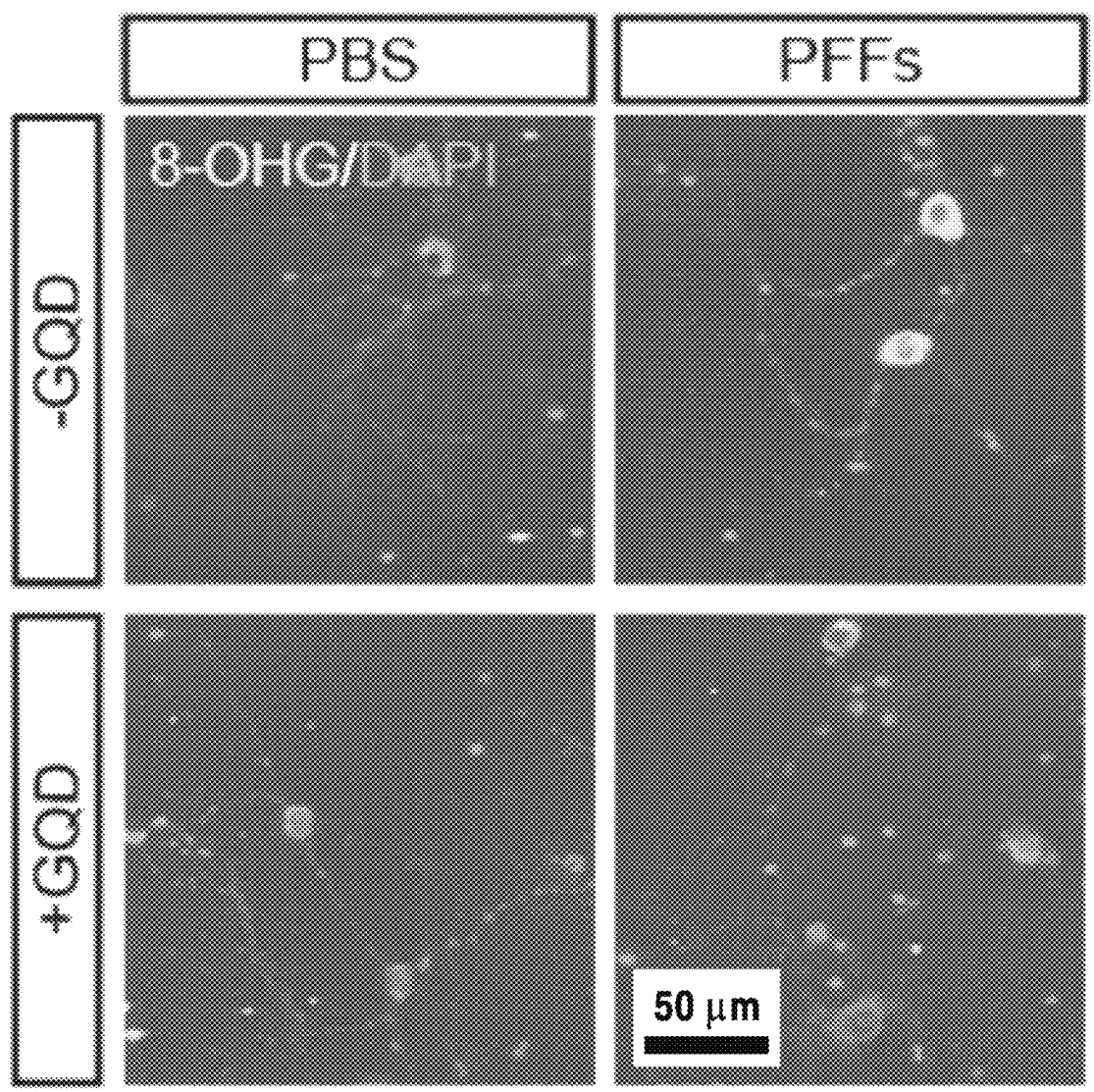

In a test of whether the graphene nanostructure used herein inhibits generation of reactive oxygen species in neurons through a mechanism that inhibits mitochondrial dysfunction caused by fibrillated proteins, primarily cultured neurons were stained with 8-OHG (8-oxo-2'-deoxyguanosine as a main product of DNA oxidation) and then analyzed (FIG. 7A). As can be seen from FIG. 7A, it was observed that the amount of 8-OHG generated by the influence of reactive oxygen species remarkably decreased by addition of the graphene nanostructure. A test of mitochondrial dysfunction was confirmed through a basal respiratory rate and a maximal respiratory rate of a cell, and mitochondrial Complex I activity assay (FIG. 7B). As shown in the graph of FIG. 7B, it was observed that when only PFFs were injected into neurons, a respiratory rate of mitochondria remarkably decreased and Complex I activity also decreased, and when GQDs and PFFs were injected into the neurons, the respiratory rate recovered to a normal level. The result of analysis of mitochondrial dysfunction through this test is considered important since it corresponds to the neuron survival rate shown in FIG. 6B.

Test Example 2

Figure 8A:
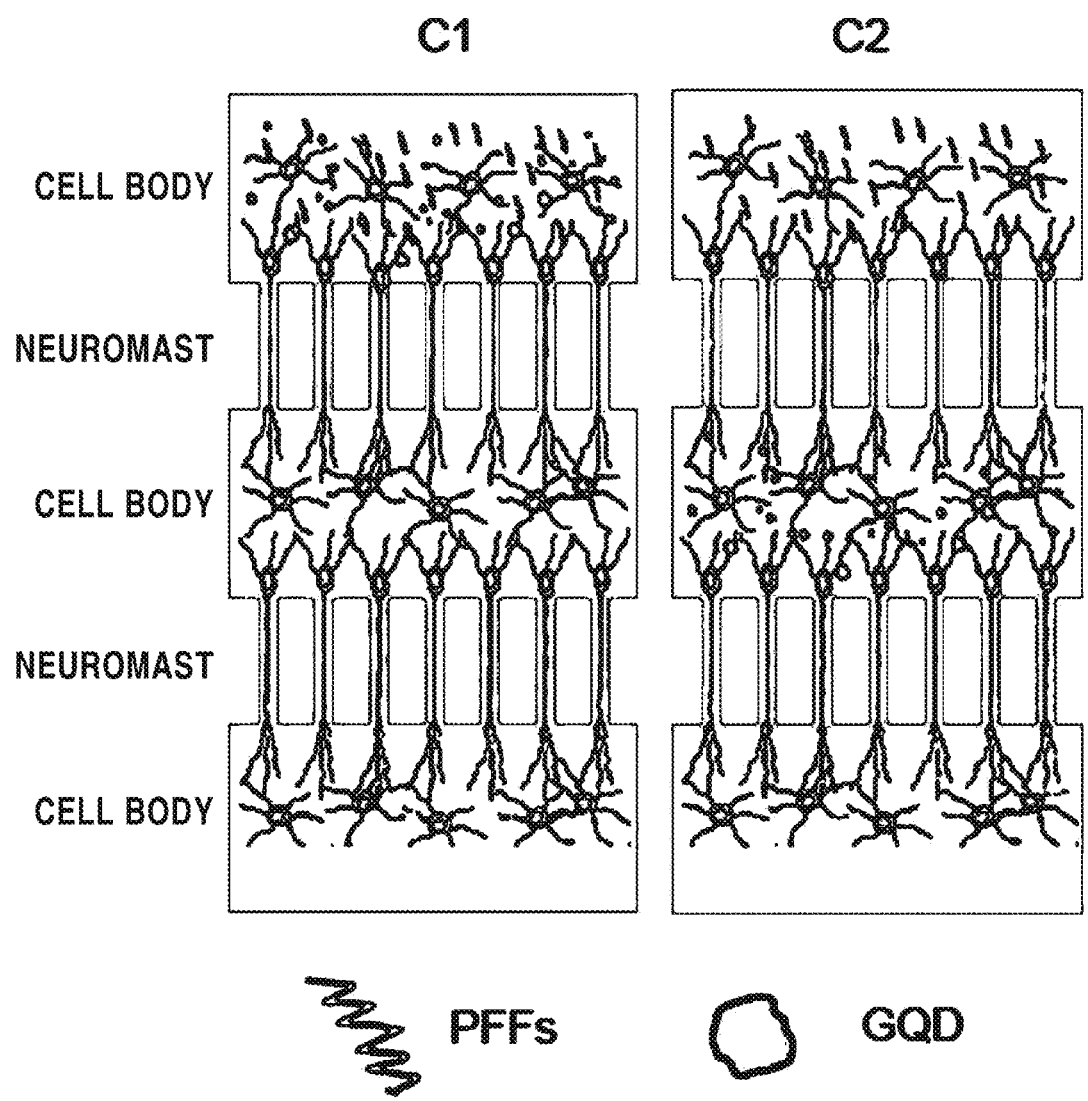
FIG. 8A and FIG. 8B provide (A) schematic diagrams of a test for confirming a-syn transition inhibition of a graphene nanostructure in accordance with an example of the present disclosure and (B) images showing the result thereof.
Figure 8B:
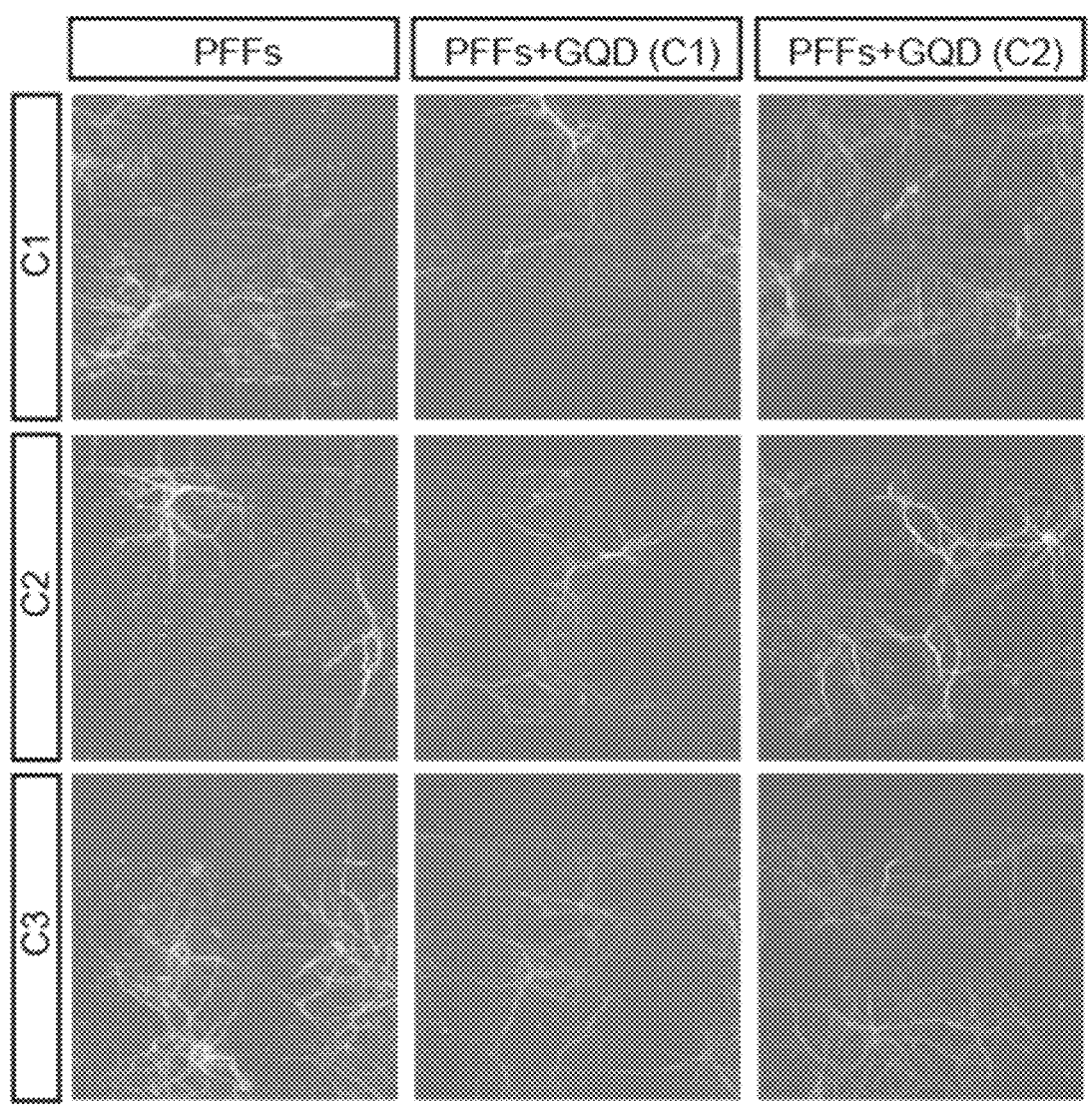

It is important to simply inhibit fibrillation and increase a neuron survival rate, but it is very important to inhibit transition to adjacent neurons in order to treat neurodegenerative diseases and slow the progress of the neurodegenerative disease. In order to confirm this fact, a microfluidic device was set up and it was checked which chamber GQDs should be put into in order to inhibit transition. FIG. 8A provides schematic diagrams of the test and FIG. 8B shows the result of the test. In case of C1 (Chamber 1), GQDs were injected into neurons in a first chamber and in case of C2 (Chamber 2), GQDs were injected into neurons in a second chamber, and then, transition of fibrillation of alpha-synuclein to adjacent neurons was observed. In a positive control group including only PFFs without GQDs, it was observed that a fibrillated alpha-synuclein was transmitted to Chambers 1 to 3. Secondly, in a device in which GQDs were put into a first neuron, fibrillation was not well developed from the first, and, thus, fibrillation of alpha-synuclein was rarely observed from second and third neurons. Finally, in a device in which GQDs were put into an intermediate neuron, fibrillation was developed to some degree in the first chamber, and the amount of fibrillation was noticeably decreased in the second neuron where the GQDs were included, and in the last neuron, it was observed that fibrillation was hardly developed. It is deemed that a difference in the degree of initial fibrillation between this device and a device which is the positive control group including only PFFs without GQDs is an error inherent in the device and caused by incomplete separation of GQDs from each neuron in the device.

Test Example 3

A sampling was performed in the same manner as an intracellular experiment (1 μg/ml GQDs and 1 μg/ml PFFs were incubated at 37° C. and then sampled on a silica substrate) and fibrillation inhibition of GQDs was analyzed using an OM (optical microscope), and as a result thereof, when only PFFs were incubated, a large lump expected as an aggregate of fibrils was observed (FIG. 9A and FIG. 9B), whereas when PFFs and GQDs were incubated, GQDs and alpha-synuclein oligomers were shown as being tangled (FIG. 9C and FIG. 9D). In the present result, the total amount of alpha-synuclein and GQDs was excessive and the images were not sufficiently clear to distinctly show the structures thereof, but it could be seen that the results of the two samples were definitely different from each other.

A sampling was performed in the same manner as the sampling for OM analysis and fibrillation inhibition of GQDs was analyzed using an AFM (atomic force microscope), and as a result thereof, when only PFFs were incubated, a lewy body formed by aggregation of fibrils and PFFs was observed (FIG. 10B), whereas when PFFs and GQDs were incubated, GQDs and alpha-synuclein oligomers were shown as being tangled (FIG. 10D).

Figure 11A:
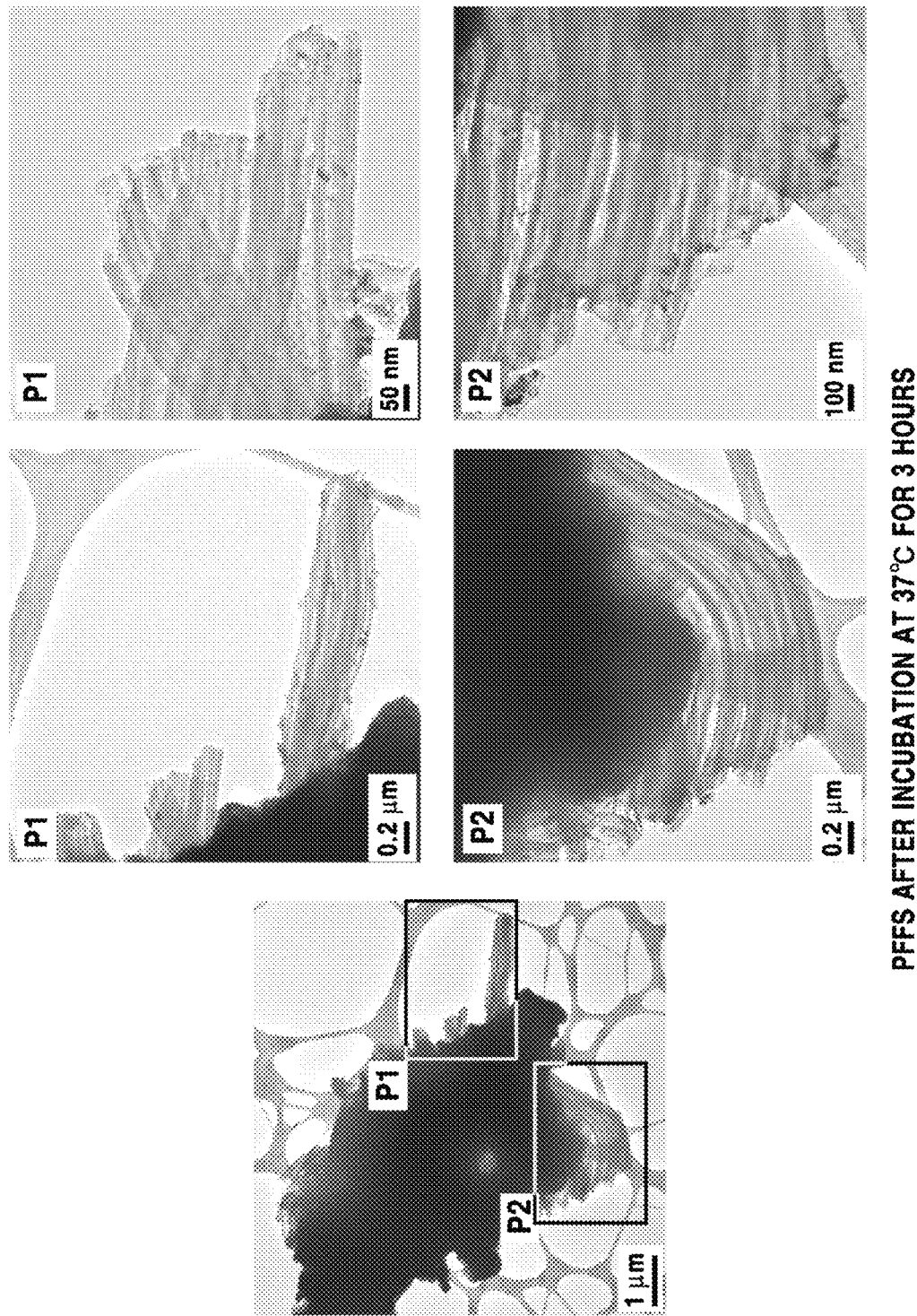
FIG. 11A and FIG. 11B show the result of high-resolution TEM analysis of fibrillation inhibition of a graphene nanostructure in accordance with an example of the present disclosure.
Figure 11B:
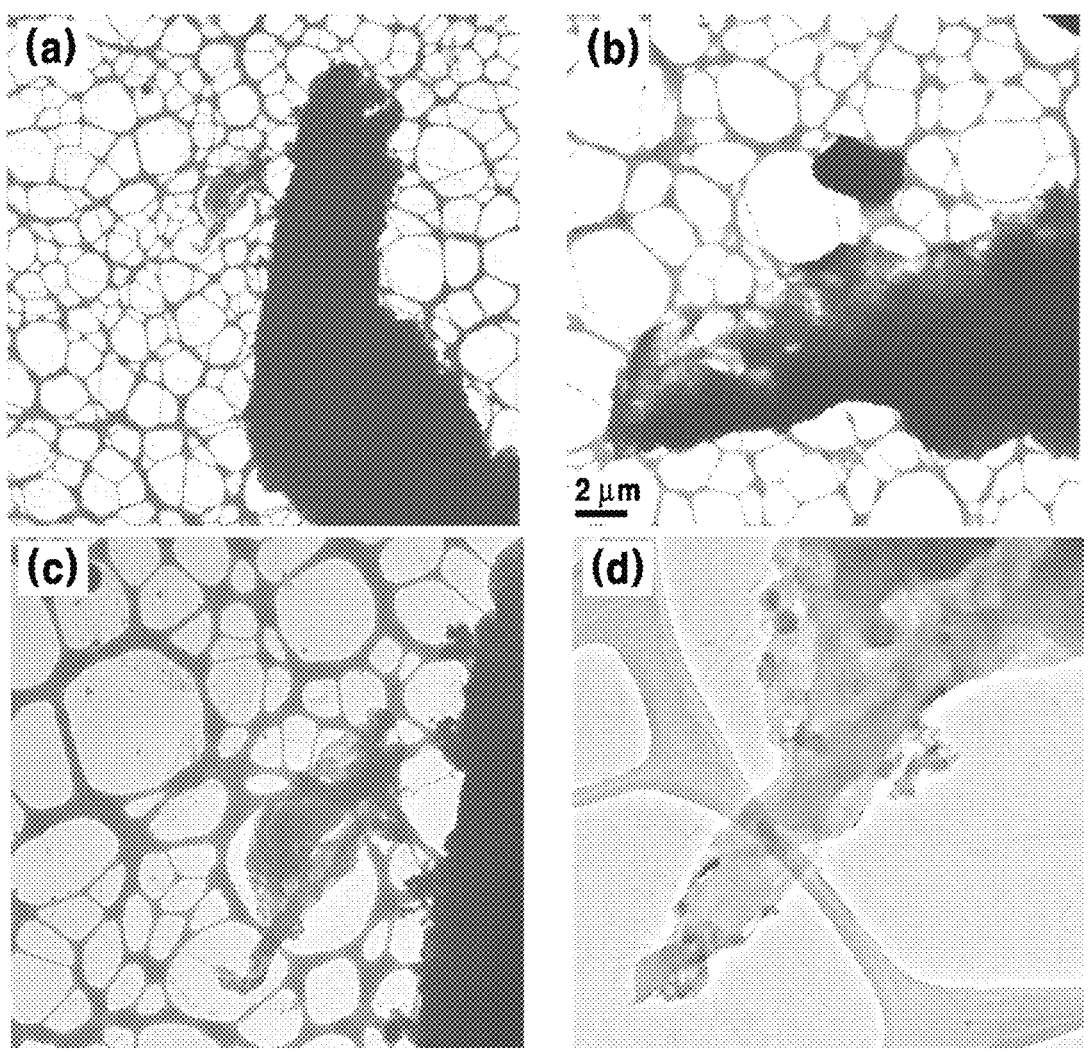

A sampling was performed on a TEM (transmission electron microscopy) grid in the same manner as the sampling for OM and AFM analyses, and an analysis was conducted using a high-resolution transmission electron microscope. FIG. 11A shows data obtained by sampling PFFs only on the TEM grid and conducting an analysis. As can be seen from the images, a very thick and long fibril bundle was observed. Meanwhile, in a sample in which GQDs were also included, as shown in the AFM image, GQDs and alpha-synuclein oligomers were shown as being tangled (FIG. 11B).

Figure 9:
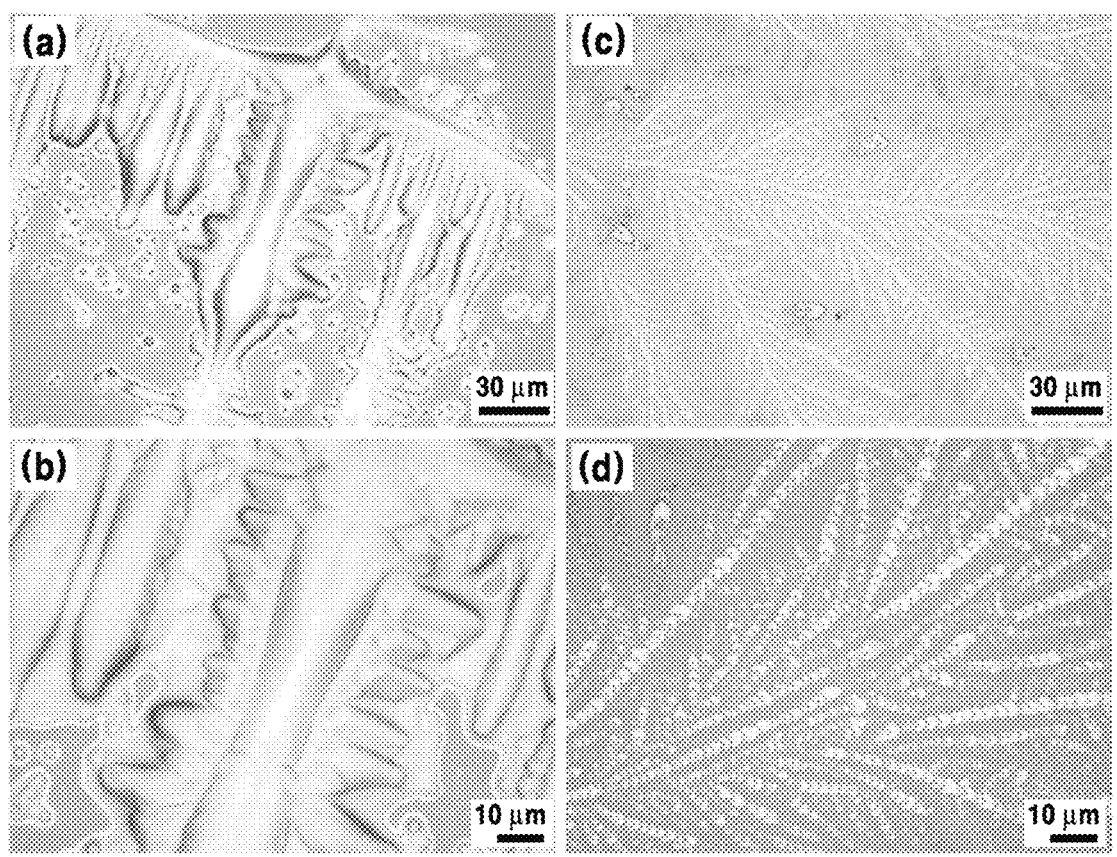
FIG. 9 shows the result of TEM analysis of fibrillation inhibition of a graphene nanostructure in accordance with an example of the present disclosure.
Figure 10:
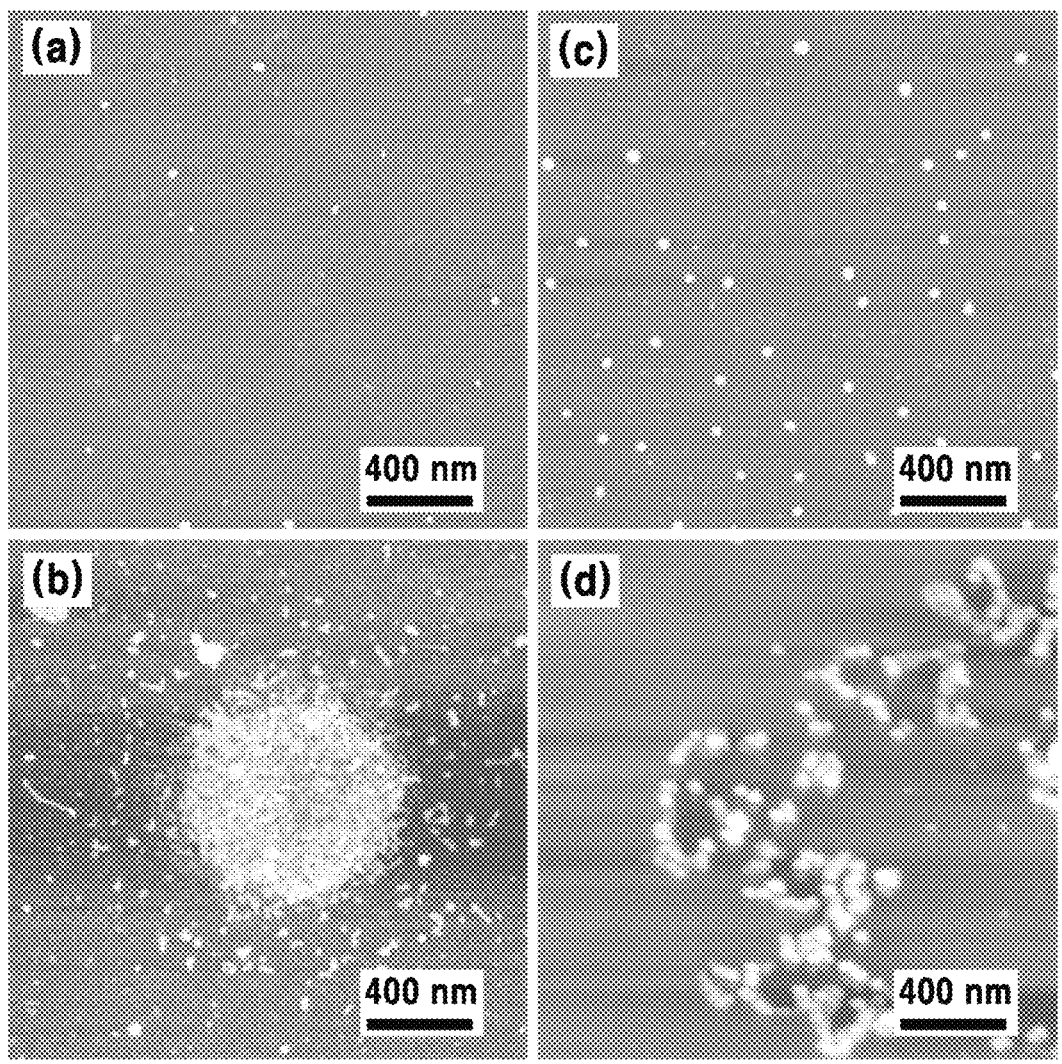
FIG. 10 shows the result of AFM analysis of fibrillation inhibition of graphene quantum dots in accordance with an example of the present disclosure.
Figure 12:
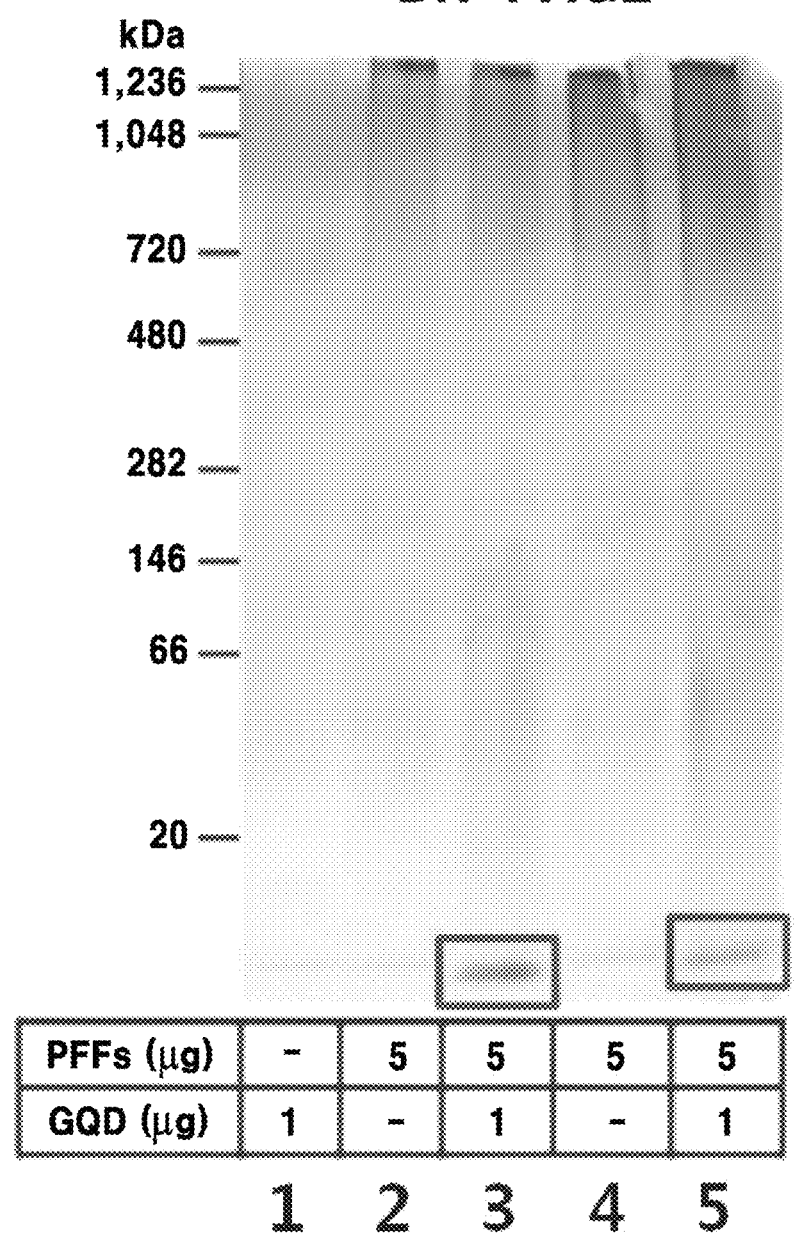
FIG. 12 shows the result of BN-PAGE analysis on PFFs after injection of a graphene nanostructure in accordance with an example of the present disclosure.

The images shown in FIG. 9 to FIG. 11 showed a marked difference between injection or non-injection of GQDs with PFFs, but these images were obtained in a dried state and thus could not show the exact state of PFFs after injection of GQDs. For more detailed analysis, BN-PAGE (blue native polyacrylamide gel electrophoresis) was performed, and a result thereof was surprising (FIG. 12). In FIG. 12, Column 1 is about a negative control group in which only GQDs are included, Columns 2 and 4 are about samples in which only PFFs are included, and Columns 3 and 5 are about samples in which both PFFs and GQDs are included, and as a result of gel insertion, it could be seen that when GQDs were injected, a strong band was detected from an area corresponding to alpha-synuclein monomers (14.46 kDa). This is very important data showing that when GQDs are added to PFFs, fibrillation of PFFs can be inhibited and PFFs are returned to monomers.

Test Example 4

The GQDs prepared in Preparation Example 1 and a Congo Red solution (control group) were irradiated with infrared rays and fluorescence was photographed in the dark, and a result thereof was as shown in FIG. 13.

Figure 14:
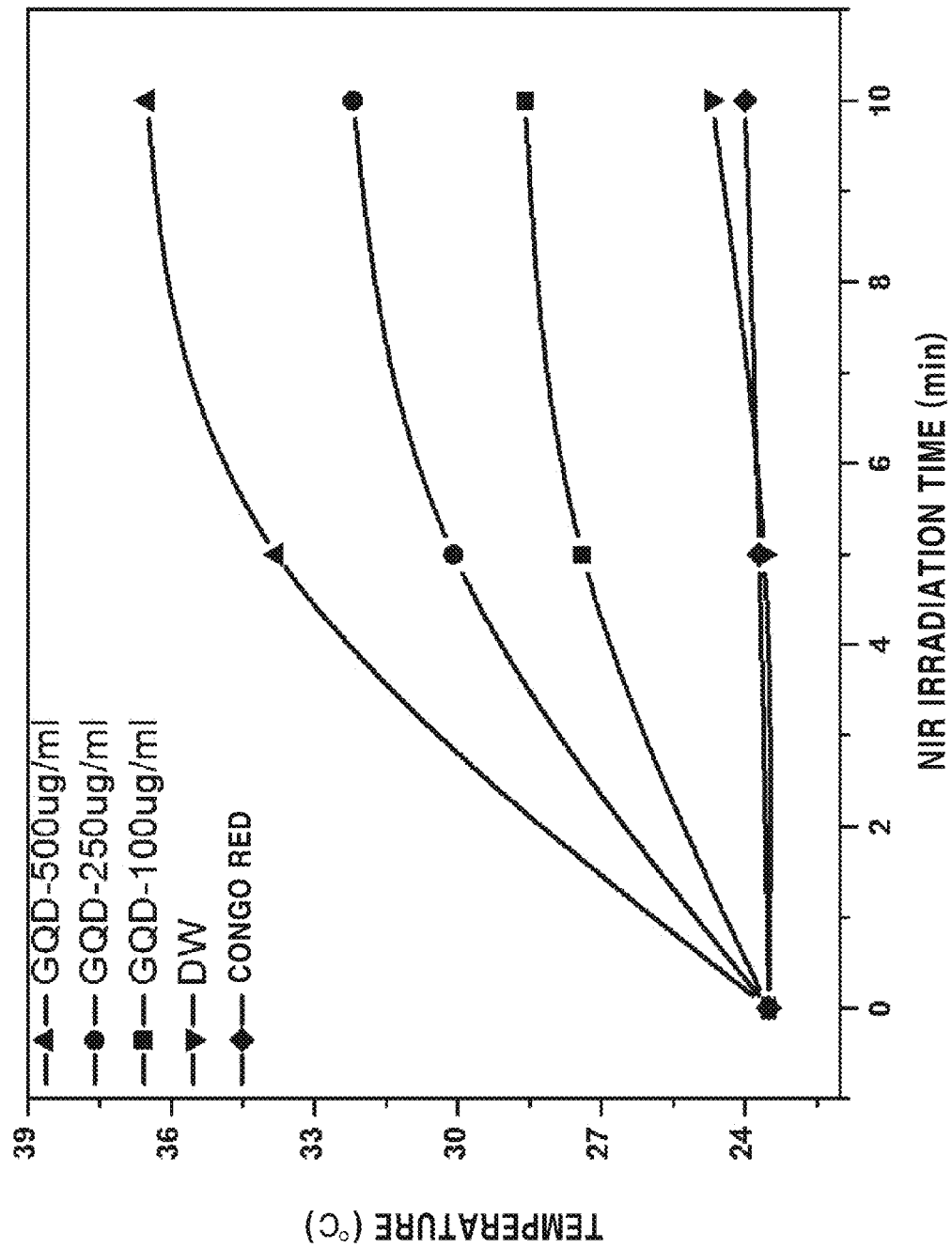
FIG. 14 is a graph showing photothermal characteristics of a graphene nanostructure in accordance with an example of the present disclosure.

Further, FIG. 14 shows that when a NIR laser was irradiated, the GQDs showed a higher photothermal effect than Congo Red or distilled water and was increased in temperature depending on the concentration of GQDs (500 μg/mL, 250 μg/mL, 100 μg/mL) as the concentration of the GQDs was increased.

Test Example 5

A FT-IR analysis and a fluorescence measurement were performed using various samples (GQDs, Sample 1, Sample 2, and Sample 3 prepared in Preparation Examples 1 and 2, and a Congo Red solution as a comparative example).

Figure 15:
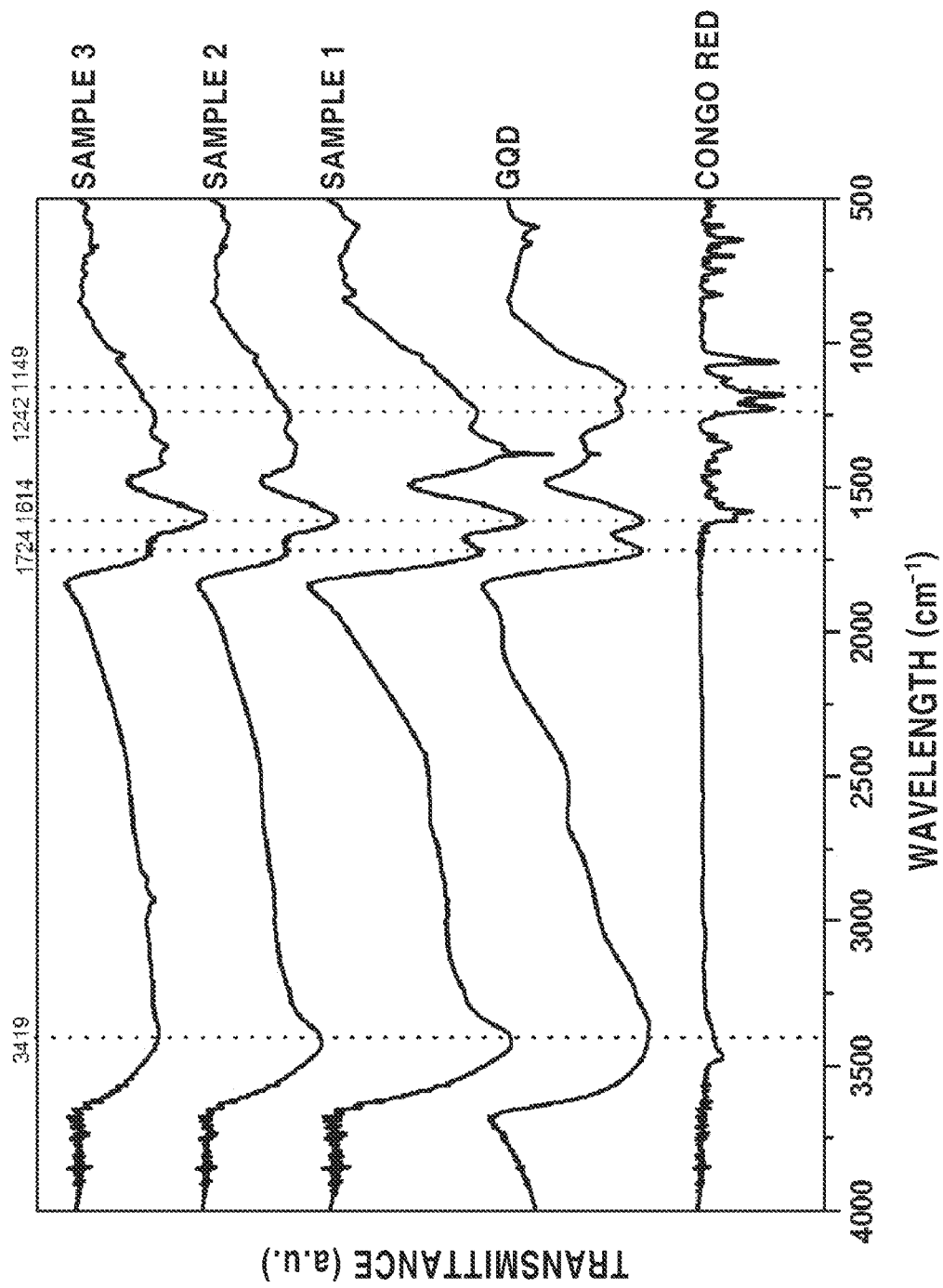
FIG. 15 shows FT-IR spectra of samples prepared in accordance with an example of the present disclosure.

Referring to FIG. 15 showing FT-IR spectra, at a —$NH_2$ peak 3419 $cm^{-1}$ of Congo Red, the peak decreased as the concentration of Congo Red increased, and even at a carboxyl group (—COOH) peak 1710 $cm^{-1}$ of a terminal of GQDs, the peak decreased as the concentration of Congo Red increased, and a peptide bond (—CONH) peak 1660 $cm^{-1}$ was gradually formed by conjugation of GQDs and Congo Red, and an aromatic C=C peak 1614 $cm^{-1}$ was maintained in all of the samples as expected.

Figure 16:
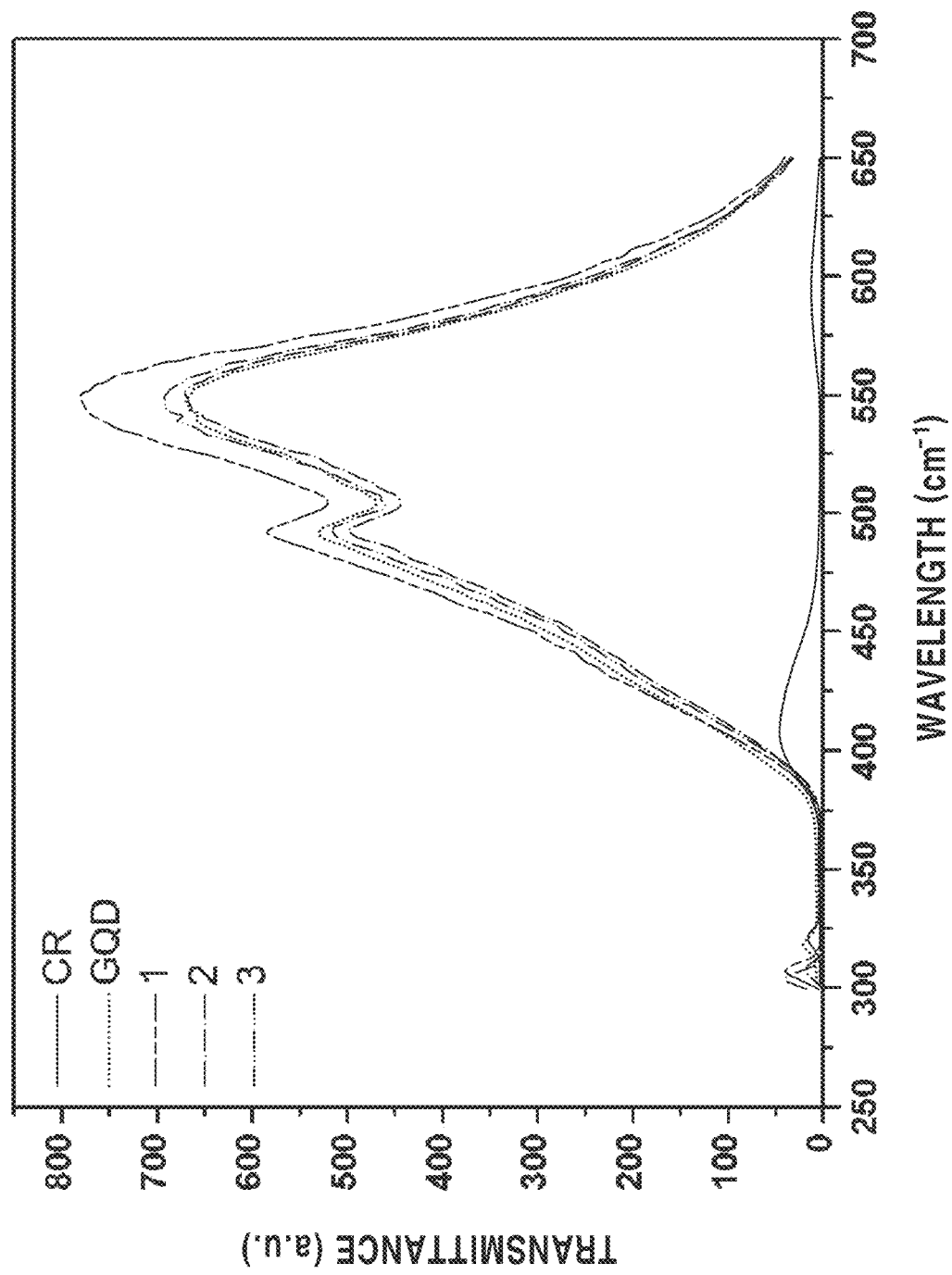
FIG. 16 shows the result of fluorescence measurement on samples prepared in accordance with an example of the present disclosure.

Meanwhile, fluorescences of the samples depending on a wavelength were measured as shown in FIG. 16. Herein, Congo Red was used as a control group, and Sample 1 showed the highest fluorescence peak.

The above description of the present disclosure is provided for the purpose of illustration, and it would be understood by those skilled in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

What is claimed is:

1. A method for treating a neurodegenerative disease, comprising administering to a patient having a neurodegenerative disease and in need thereof an effective amount of a composition comprising graphene quantum dots, wherein the graphene quantum dots have a lateral size of about 3 to 5 nm and an average height of about 5 to 15 nm, wherein the graphene quantum dots are not bound at terminal functional groups to other moieties.

2. The method of claim 1, wherein the composition further comprises a pharmaceutically acceptable carrier or excipient.

3. The method of claim 2, wherein the pharmaceutically acceptable carrier or excipient comprises a member selected from the group consisting of petroleum jelly, lanolin, polyethylene glycol, alcohol, and combinations thereof.

4. The method of claim 1, wherein the graphene quantum dots inhibit fibril formation caused by protein misfolding.

5. The method of claim 1, wherein the graphene quantum dots inhibit transition of misfolded proteins.

6. The method of claim 1, wherein the graphene quantum dots are not accumulated in the body.

7. The method of claim 1, wherein the graphene quantum dots show a photothermal effect upon irradiation by a far-infrared laser.

8. The method of claim 1, wherein the patient exhibits detectable symptoms of a neurodegenerative disease.

9. The method of claim 8, wherein the neurodegenerative disease comprises a member selected from the group consisting of Alzheimer's disease, Parkinson's disease, Huntington's chorea, HIV dementia, stroke, senile systemic amyloidosis, primary systemic amyloidosis, secondary systemic amyloidosis, type II diabetes, amyotrophic amyloidosis, hemodialysis-related amyloidosis, transmissible spongiform encephalopathy, and multiple sclerosis.

10. A method for treating a neurodegenerative disease, consisting of administering to a patient having a neurodegenerative disease and in need thereof an effective amount of a composition of graphene quantum dots and a pharmaceutically acceptable carrier or excipient, wherein the graphene quantum dots have a lateral size of about 3 to 5 nm and an average height of about 5 to 15 nm, wherein the graphene quantum dots are not bound at terminal functional groups to other moieties.

11. The method of claim 10, wherein the patient exhibits detectable symptoms of a neurodegenerative disease.

12. A method for treating a neurodegenerative disease, comprising administering to a patient having a neurodegenerative disease and in need thereof an effective amount of a composition of graphene quantum dots and a pharmaceutically acceptable carrier or excipient, wherein the graphene quantum dots have a lateral size of about 3 to 5 nm and an average height of about 5 to 15 nm, wherein the graphene quantum dots are not bound at terminal functional groups to other moieties.

13. The method of claim 12, wherein the patient is not subjected to photothermal treatment after administration of said graphene quantum dots.

14. The method of claim 12, wherein the patient exhibits detectable symptoms of a neurodegenerative disease.

* * * * *